US012778551B2

(12) United States Patent
Vercesi et al.

(10) Patent No.: US 12,778,551 B2
(45) Date of Patent: Nov. 3, 2026

(54) HIGH DENSITY PMUT ARRAY ARCHITECTURE FOR ULTRASOUND IMAGING

(71) Applicant: STMicroelectronics International N.V., Geneva (CH)

(72) Inventors: Federico Vercesi, Milan (IT); Giorgio Allegato, Monza (IT); Tarek Afifi Afifi, Milan (IT); Sonia Costantini, Missaglia (IT)

(73) Assignee: STMicroelectronics International N.V., Geneva (CH)

( * ) Notice: Subject to any disclaimer, the term of this patent is extended or adjusted under 35 U.S.C. 154(b) by 884 days.

(21) Appl. No.: 18/123,602

(22) Filed: Mar. 20, 2023

(65) Prior Publication Data

US 2024/0315671 A1 Sep. 26, 2024

(51) Int. Cl.
*A61B 8/00* (2006.01)

(52) U.S. Cl.
CPC .............. *A61B 8/4483* (2013.01); *A61B 8/52* (2013.01)

(58) Field of Classification Search
CPC ....... A61B 8/4483; A61B 8/52; B06B 1/0622; B06B 1/0666; G01H 11/08
See application file for complete search history.

(56) References Cited

U.S. PATENT DOCUMENTS 7,405,637 B1 * 7/2008 Mehta .................. H01P 1/2056 333/207
7,449,821 B2 * 11/2008 Dausch ................. B06B 1/0622 310/365
(Continued)

FOREIGN PATENT DOCUMENTS

CN 101578686 A 11/2009
CN 104837096 A 8/2015
(Continued)

OTHER PUBLICATIONS

Shin, Eunjung, et al.: "Development of a High-Dendity Piezoelectric Micromachined Ultrasonic Transducer Array Based on Patterned Aluminum Nitride Thin Film," Micromachines 2020, 11, 623; doi:10.3390/mi11060623, 10 pgs.
(Continued)

*Primary Examiner* — J. San Martin
(74) *Attorney, Agent, or Firm* — Crowe & Dunlevy LLC

(57) ABSTRACT

A PMUT includes a substrate being doped and having a plurality of conductive vias formed therein, each conductive via formed of a portion of the substrate extending completely from a back side of the substrate to a front side of the substrate and being encircled by an isolating structure that electrically isolates that portion of the substrate from other portions of the substrate. An insulating layer stacked on the front side of the substrate and has through-holes therein over the plurality of conductive vias. An interconnection layer is stacked on the insulating layer and is connected to the plurality of conductive vias. A membrane carried is by the interconnection layer and underlying substrate, the membrane being shaped so as to delimit a chamber. A piezoelectric stack formed on the membrane over the chamber and vibrates the membrane in response to application of an alternating voltage to the piezoelectric stack.

19 Claims, 17 Drawing Sheets

(56) References Cited

U.S. PATENT DOCUMENTS

| | | | | |
|---|---|---|---|---|
| 2008/0203556 | A1* | 8/2008 | Huang | H10W 20/023<br>257/E21.597 |
| 2011/0115333 | A1* | 5/2011 | Ezaki | B06B 1/0292<br>310/300 |
| 2015/0054095 | A1 | 2/2015 | Jeong et al. | |
| 2015/0137285 | A1* | 5/2015 | Shim | B81C 1/00301<br>257/416 |
| 2016/0221038 | A1* | 8/2016 | Johnson | B81C 1/00301 |
| 2018/0154393 | A1 | 6/2018 | Viegas et al. | |
| 2020/0250393 | A1 | 8/2020 | Tsai et al. | |
| 2021/0094070 | A1 | 4/2021 | Bircumshaw et al. | |
| 2024/0286171 | A1* | 8/2024 | Bayram | B06B 1/0292 |

FOREIGN PATENT DOCUMENTS

| | | | | | |
|---|---|---|---|---|---|
| CN | 113441379 | A | | 9/2021 | |
| CN | 114130636 | A | * | 3/2022 | B06B 1/0622 |
| JP | 2012143615 | A | | 8/2012 | |

OTHER PUBLICATIONS

Zhang, Yun, et al.: "Design of AIN and PZT pMUT for High-Quality Ultrasound Imaging," 2021 IEEE, 3 pgs.
CN First Office Action and Search Report for counterpart CN Appl. No. 202410307299.9, report dated Jun. 26, 2026, 6 pgs.

* cited by examiner

HIGH DENSITY PMUT ARRAY ARCHITECTURE FOR ULTRASOUND IMAGING

TECHNICAL FIELD

This disclosure is related to the field of piezoelectric micromachined ultrasound transducers (PMUTs) and, in particular, to a design for an array of PMUTs.

BACKGROUND

Ultrasound is used today in a variety of applications for imaging and sensing. Some of the applications for ultrasound technology utilize micromachined ultrasound transducers (MUTs). MUTs include both capacitive micromachined ultrasound transducers (CMUTs) and piezoelectric micromachined ultrasound transducers (PMUTSs).

A CMUT element can be thought of as a miniaturized capacitor formed of a thin metallized membrane suspended over a cavity, with the cavity floor being formed by a rigid metallized substrate. When a DC voltage is applied between the membrane and substrate, the membrane is attracted toward the substrate by electrostatic forces between the metallic layer on the membrane and the substrate. Thus, by applying a suitable AC voltage between the metallic layer and the substrate, oscillation of the membrane is induced, and an ultrasound wave is generated.

A PMUT element is formed by a membrane suspended over a cavity carrying a layer of piezoelectric material sandwiched between thin electrode layers. The sandwiching of the piezoelectric material between the thin electrode layers can be thought of as a parallel plate capacitor with a piezoelectric layer between the plates. In operation, a voltage is applied across the electrodes, resulting in a lateral strain being induced in the membrane via the piezoelectric effect causing movement of the piezoelectric layer. By applying a suitable AC voltage between the electrodes oscillation of the membrane is induced and an ultrasound wave is generated.

In medical imaging application, an ultrasound imaging device including a transducer is used to transmit ultrasound waves into the body. The ultrasound waves echo off structures within the body and return to the ultrasound imaging device to be detected by a detector therein. From these returned echoes, an image of the desired portion of the body may be formed.

It is desired for an ultrasound imaging device to be capable of producing a wide bandwidth of ultrasound waves. For example, low-frequency ultrasound waves (e.g., 1 MHz) are used in the imaging of deeper structures (e.g., at a depth of 40 cm), while high-frequency ultrasound waves (e.g., 10 MHz) are used in the imaging of shallower structures (e.g., at a depth of 1 cm).

To produce an ultrasound imaging device capable of meeting these performance specifications while providing for high resolution images, a high-density array of MUTs is desired within the device. An array of CMUT elements can be tightly packed due to the lack of piezoelectric electrodes and the accompanying electrical interconnections between layers. However, CMUT based devices lack certain advantages present in PMUT devices. PMUT devices, while possessing certain advantages for some applications, may be difficult to form in high density arrays, with this difficulty arising in part from the use of vias to provide voltage to the piezoelectric electrodes.

Given this, further development into the area of PMUT devices is needed to enable the formation of high-density arrays of PMUT devices.

SUMMARY

Disclosed herein is a device including a piezoelectric micromachined ultrasound transducer (PMUT). The PMUT includes: a substrate, the substrate having a plurality of conductive vias formed therein, each conductive via potentially including a portion of the substrate or a conductive layer (e.g., doped polysilicon) extending completely from a back side of the substrate to a front side of the substrate and being encircled by an isolating structure that electrically isolates that portion of the substrate from other portions of the substrate; an insulating layer stacked on the front side of the substrate and having through-holes defined therein over the plurality of conductive vias; an interconnection layer stacked on the insulating layer and being directly electrically connected to the plurality of conductive vias; a membrane carried by the interconnection layer and underlying substrate, the membrane shaped so as to delimit a chamber defined on a top side and sidewalls by the membrane and defined on a bottom side by the insulating layer; and a piezoelectric stack formed on the membrane over the chamber and configured to vibrate the membrane in response to application of an alternating voltage to the piezoelectric stack.

The substrate may be a highly doped silicon substrate. The isolating structure of each via may be comprised of oxide. The insulating layer may be an oxide layer.

Each PMUT may further include an insulating layer on the back side of the substrate, with electrodes extending through holes in the insulating layer to contact the conductive vias.

First and second conventional vias may be formed to extend through the membrane to electrically connect the piezoelectric stack to the interconnection layer.

The membrane may include: a support layer carried by the interconnection layer and underlying substrate and being shaped so as to delimit the chamber; a permeable polysilicon layer formed on the support layer; and a structural layer carried by the permeable polysilicon layer and underlying portions of the structural layer.

A silicon thermal oxide layer may be stacked on the membrane and carry the piezoelectric stack. The piezoelectric stack may include a first electrode formed on the silicon thermal oxide layer, a piezoelectric layer formed on the first electrode, and a second electrode formed on the piezoelectric layer. The first electrode may be electrically connected to the interconnection layer through a first conventional via extending through the membrane and silicon thermal oxide layer. The second electrode may be electrically connected to the interconnection layer through a second conventional via extending through the membrane and silicon thermal oxide layer.

Also disclosed herein is a method of making a piezoelectric micromachined ultrasound transducer (PMUT). The method includes: etching a substrate to define a plurality of conductive columns within the substrate, with the etch defining a ring around each conductive column; depositing an isolating material within each ring to thereby define a plurality of conductive vias, each conductive via including one of the conductive columns and being isolated by the isolating material within the ring associated with that conductive via; depositing an insulating layer on a front side of the substrate; forming an interconnection layer on the insulating layer and extending through the insulating layer to make electrical contact with the plurality of conductive vias; depositing a sacrificial layer on the interconnection layer and patterning the sacrificial layer; forming a membrane layer on the sacrificial layer, with portions of the membrane layer extending through the sacrificial layer to contact the interconnection layer; performing an etch release to remove the sacrificial layer, thereby defining a membrane carried by the interconnection layer and underlying substrate; depositing a ceiling layer on the membrane layer and patterning the ceiling layer; and forming a piezoelectric stack on the ceiling layer and exposed portions of the membrane over a chamber delimited in the membrane.

The sacrificial layer may be patterned to define through-holes in therein exposing portions of the interconnection layer. The portions of the membrane layer that extend through the sacrificial layer may extend through the through-holes.

Forming the interconnection layer may include depositing a polysilicon layer on the insulating layer and patterning the polysilicon layer.

Performing the etch release may include etching through-holes in the membrane layer and then performing the etch release through the through-holes in the membrane layer. The ceiling layer may extend across the through-holes etched in the membrane layer.

The etch release may be a vapor-phase hydrofluoric acid (vHF) etch.

The method may further include grinding a back side of the substrate to expose the plurality of conductive vias.

The method may further include: flipping the substrate; forming an insulating layer on the back side of the substrate and patterning the substrate to expose the plurality of conductive vias; and forming electrodes that extend through the insulating layer on the back side of the substrate to contact the exposed plurality of conductive vias.

Forming the piezoelectric stack on the membrane may include: depositing a first conductive layer on the membrane and patterning the first conductive layer to thereby form a first electrode; forming a piezoelectric layer on the first conductive layer; and depositing a second conductive layer on the piezoelectric layer, the ceiling layer, and exposed portions of the membrane layer, and patterning the second conductive layer to thereby form a second electrode.

The substrate may be a highly doped silicon substrate.

Forming the membrane layer on the sacrificial layer may include: forming a support layer on the sacrificial layer and patterning the support layer; and forming a permeable polysilicon layer on the support layer. The etch release may be performed through the permeable polysilicon layer. Forming the membrane layer further may include growing a structural layer on the permeable polysilicon layer and patterning the structural layer.

DETAILED DESCRIPTION

The following disclosure enables a person skilled in the art to make and use the subject matter disclosed herein. The general principles described herein may be applied to embodiments and applications other than those detailed above without departing from the spirit and scope of this disclosure. This disclosure is not intended to be limited to the embodiments shown, but is to be accorded the widest scope consistent with the principles and features disclosed or suggested herein.

Figure 1:
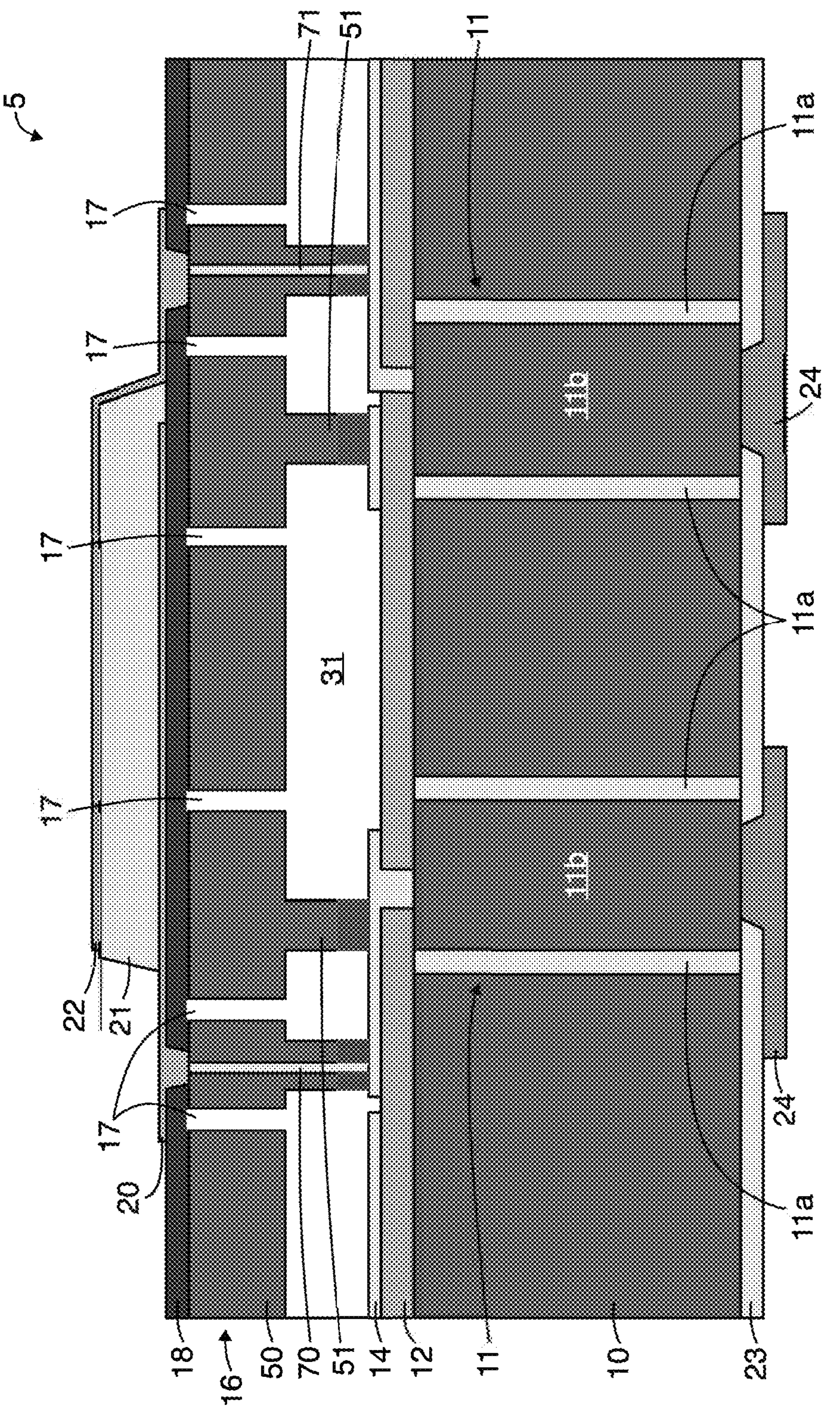
FIG. 1 is a cross sectional view of a piezoelectric micromachined ultrasound transducer (PMUT) cell disclosed herein.

Disclosed herein with reference to FIG. 1 is an individual piezoelectric micromachined ultrasound transducer (PMUT) cell 5, such as may be used in an array thereof (described in detail below). The PMUT cell 5 includes a highly doped substrate 10, for example so called red phosphorous, having vias 11 formed therein. The vias 11 are not conventional vias but are instead formed by insulating ring 11*a* surrounding portions of the substrate 10 acting as conductive columns 11*b*. This serves to decouple the diameter of the conductive portion of the vias 11 from the process used to form the vias, since here the conductive columns 11*b* are the conductive portions of their respective vias-conventionally, the diameter of the conductive portion of the vias would be limited by the filling process. This also serves to decouple the filling process for the insulating rings 11*a* from the production of the conductivity of the vias 11. Still further, the diameter of the vias 11 being wider than conventional vias provides for additional mechanical robustness, making the length of the vias 11 less of a concern for robustness than it would be with conventional designs.

An oxide layer 12 is stacked on the front side of the substrate 10, with the back face of the oxide layer 12 being in direct physical contact with the front side of the substrate 10. The oxide layer 12 may be a silicon thermal oxide (TEOS) layer having a thickness ranging from 2000 Å to 5 μm.

An interconnection layer 14 (e.g., formed of polysilicon having a thickness ranging from 1000 Å to 2 μm) is stacked on the oxide layer 12 such that its back face is in direct physical contact with the front face of the oxide layer 12. The oxide layer 12 has openings formed therein through which portions of the interconnection layer 14 extend to make direct physical and electrical contact with a conductive vias 11 embedded in the silicon substrate 10. The via can be shaped as a conductive column 11*b* such as shown in FIG. 1.

A structural layer 16 forming a membrane is carried by and in direct physical contact with the interconnection layer 14, with anchoring legs 51 of the structural layer extending downwardly from a main body 50 of the structural layer 16 to make physical contact with the front face of the interconnection layer 14. The structural layer 16 may be formed from LPCVD polysilicon, epitaxial silicon, and/or metal (e.g., aluminum, gold) having a thickness ranging from 1 μm to 100 μm.

The anchoring legs 51 of the structural layer 16 serve to space the main body 50 of the structural layer 16 apart from the interconnection layer 14. A chamber 31 is defined between exposed portions of the front face of the oxide layer 12, associated parts of the front face of the interconnection layer 14, and back face of the main body 50 of the structural layer 16.

A tetraethyl orthosilicate (TEOS) layer 18 is stacked on the front face of the membrane 16 such that its back face is in direct physical contact with the front face of the membrane 16 and covers through-holes 17 that are defined in the membrane 16. The TEOS layer 18 may have a thickness ranging from 2000 Å to 5 μm, and may be formed from other oxides instead of TEOS (e.g., thermal oxide, undoped silicon glass).

A first electrode 20 (e.g., bottom electrode) is stacked on the front face of the TEOS layer 18, and through-holes are defined in the TEOS layer 18 such that portions of the first electrode 20 extend therethrough to contact underlying portions of the front face of the membrane 16. The first electrode 20 may be formed from doped polysilicon, molybdenum, platinum, titanium platinum, and/or conductive oxides (e.g., LNO, ITO) having a thickness ranging from 200 Å to 2000 Å.

A piezoelectric layer 21 is stacked on and in direct physical contact with the front face of the first electrode 20 and an exposed portion of the front face of the TEOS layer 18. The piezoelectric layer 21 may be formed of AlN, AlScN, PZT, and/or KNN, for example, ranging in thickness from 0.3 μm to 4 μm.

A second electrode 22 (e.g., top electrode) is stacked on and in direct physical contact with the piezoelectric layer 21, with a portion of the back face of the second electrode 22 being in direct physical contact with a front face of the piezoelectric layer 21, thereby sandwiching the piezoelectric layer 21 between the first electrode 20 and second electrode 22. The second electrode 22 may be formed from molybdenum, platinum, titanium platinum, titanium tungsten, gold, aluminum, and/or conductive oxides (e.g., LNO, ITO), ranging in thickness from 200 Å to 2000 Å.

A portion of the second electrode 22 extends past the side end of the piezoelectric layer 21 to make contact with the front face of the TEOS layer 18 and to extend through an exposed portion of the TEOS layer 18 to contact an underlying portion of the membrane 16.

An insulating layer 23 is stacked on the back side of the substrate 10 such that its back face is in direct physical contact with the back side of the substrate. The insulating layer 23 may be formed of TEOS, USG, and/or silicon dioxide, ranging in thickness from 2000 Å to 2 μm.

Through-holes are defined in the insulating layer 23 through which back side electrodes 24 extend to make physical and electrical contact with the conductive columns 11*b* of the vias 11.

Electrical contact is made from the back side electrode 24 (on the left) to the electrode 20 through the conductive column 11*b* (left side), through the interconnection layer 14 to a conventional conductive via 70 which extends through the structural layer 16 and through TEOS layer 18 to reach the bottom of the electrode 20.

Similarly, electrical contact is made from the back side electrode 24 (on the right) to the electrode 22 through the conductive column 11*b* (right side), through the interconnection layer 14 to a conventional conductive via 71 which extends through the structural layer 16 and through TEOS layer 18 to reach the bottom of electrode 22.

Figure 18:
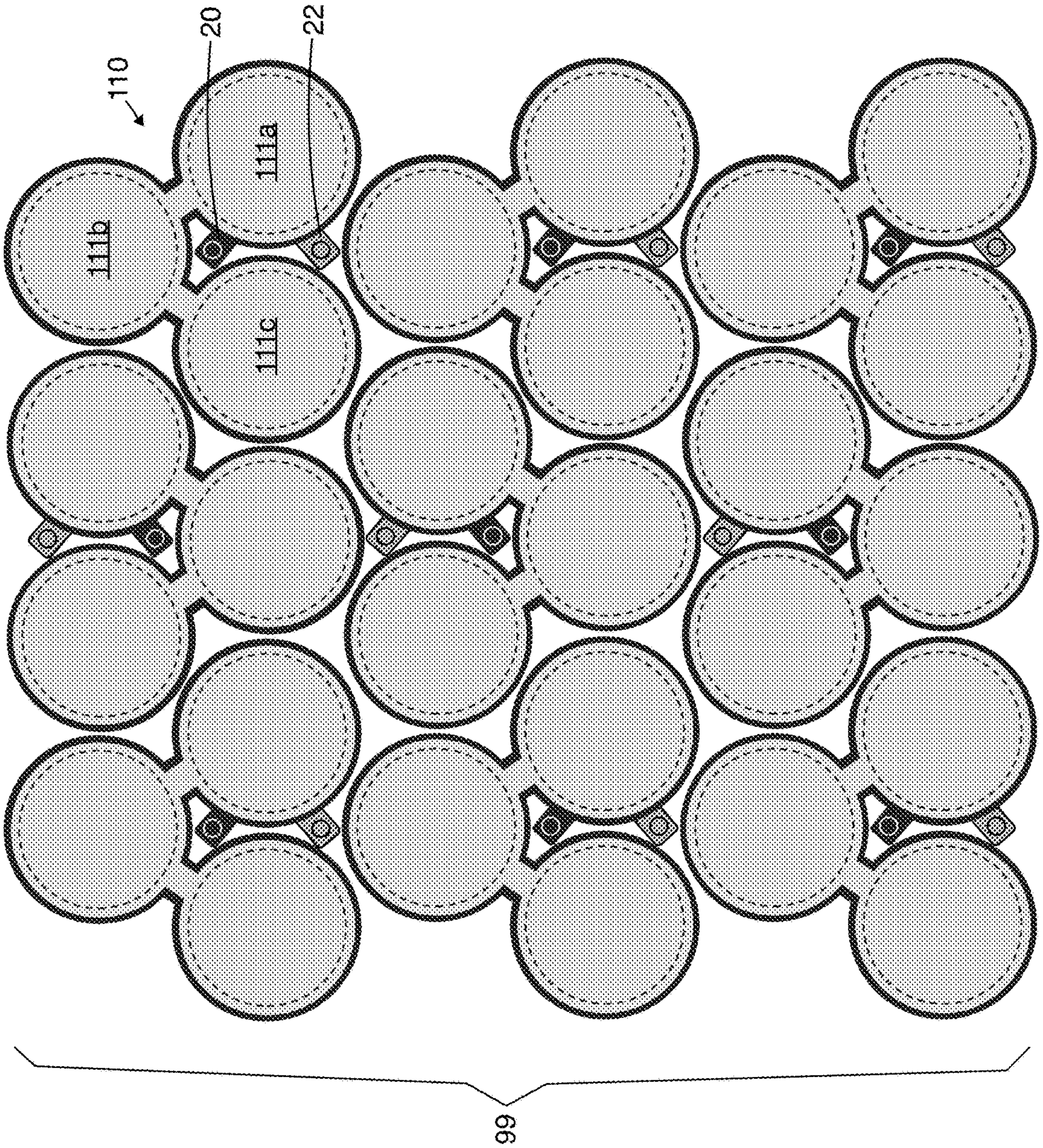
FIG. 18 is a top view of an array of PMUT cells formed using the PMUT cells of FIG. 1 or 14.
Figure 19:
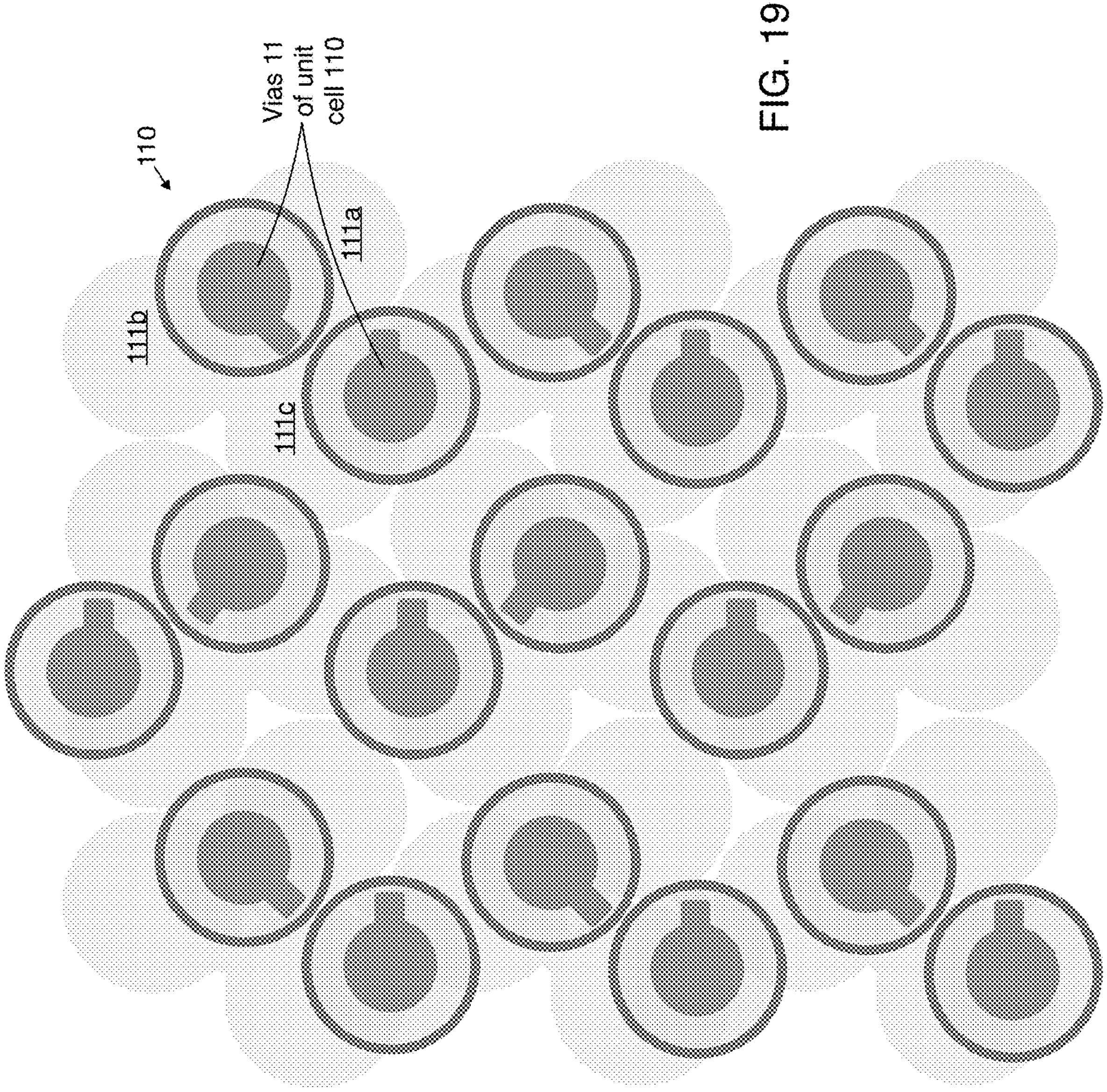
FIG. 19 is a diagrammatical view of the array of PMUT cells of FIG. 18, showing the vias that extend through the substrate.

As explained above, the PMUT cell 5 may be used to form an array 99 of PMUT cells 5. This array is now described with reference to FIGS. 18-19. The array 99 may be formed of multiple unit cells, with each unit cell containing multiple individual PMUT cells having their respective first and second electrodes connected that each PMUT cell of the unit cell is activated simultaneously and identically. A sample unit cell 110 is shown in FIG. 18, formed of individual PMUT cells 111*a*-111*c*. The top electrodes of PMUT cells 111*b* and 111*c* are connected to the top electrode 22 of PMUT cell 11*a*, and the bottom electrodes of PMUT dells 111*b* and 111*c* are connected to the bottom electrode 20 of PMUT cell 111*a*. The PMUT cells 111*b* and 111*c* therefore lack vias 11 because the electrical connections for their top electrodes 22 and bottom electrodes 20 are through the top electrode 22 and bottom electrode 20 (and their associated vias) of PMUT cell 11*a*. Thus, each unit cell is driven by a total of two vias 11, saving space, as can be observed in FIG. 19.

As will be appreciated, each unit cell may include any number of individual PMUT cells, and the array may contain any number of unit cells. In addition, instead of utilizing unit cells comprised of multiple individual PMUT cells, the array may be formed of individual PMUT cells not arranged into unit cells, each with its own dedicated vias, and arranged into an array format.

In operation, drive circuitry (not shown) applies a suitable AC voltage across the electrodes 20 and 22, resulting in oscillating lateral strain being induced in the membrane 16 via the piezoelectric effect. The vibration of the membrane 16 generates ultrasound waves of the desired frequency, based upon the applied AC voltage. Also during operation, a sensor (not shown) detects ultrasound waves originally emitted by the PMUT cell 5 that have travelled into the target (e.g., human body or other suitable target) and reflected off sub-surface structures to return to the sensor. A processing device (not shown) reads the ultrasound reflection data from the sensor and performs suitable data processing to generate a displayable image of the target being sensed and the subsurface structures in the target off which the ultrasound waves reflected.

Figure 2:
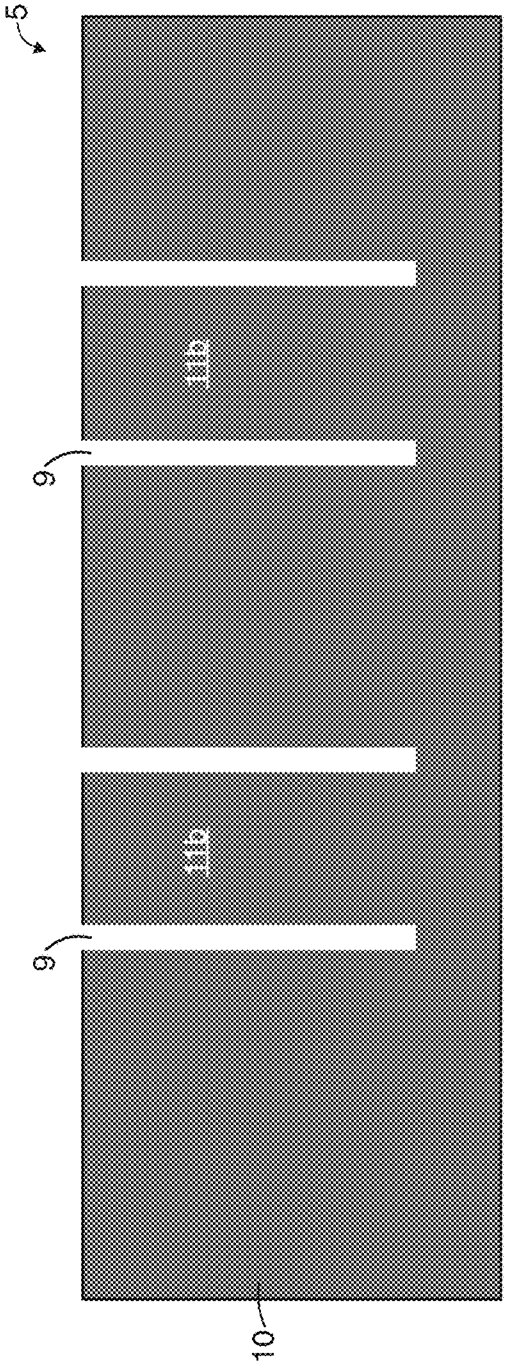
FIGS. 2-13 are a series of cross-sectional views showing the process flow for forming the PMUT cell of FIG. 1.

A process flow for forming the PMUT cells 5 is now described with initial reference to FIG. 2. Beginning with a highly doped red phosphorous substrate 10, a deep trench etch is performed to define rings 9 in the substrate 10 and extending from the front side of the substrate 10 toward the back side of the substrate 10. This etching sets the perimeters of the vias 11 to be formed and defines the conductive columns 11*b*.

Figure 3:
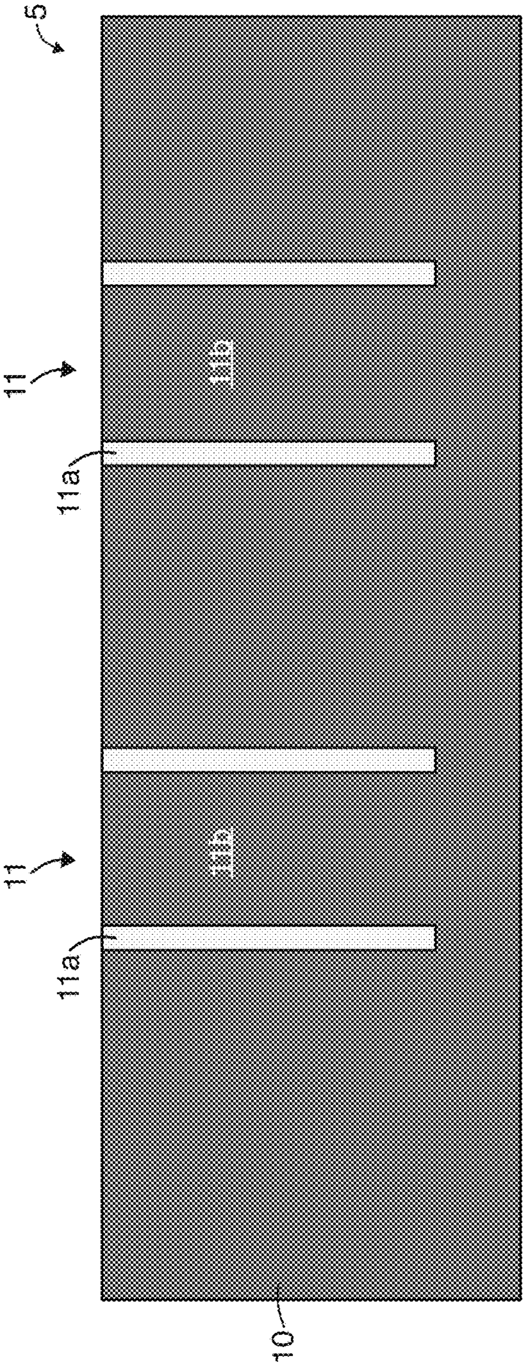

Next, as shown in FIG. 3, the rings 9 are filled with oxide to electrically isolate the conductive columns 11*b*.

Figure 4:
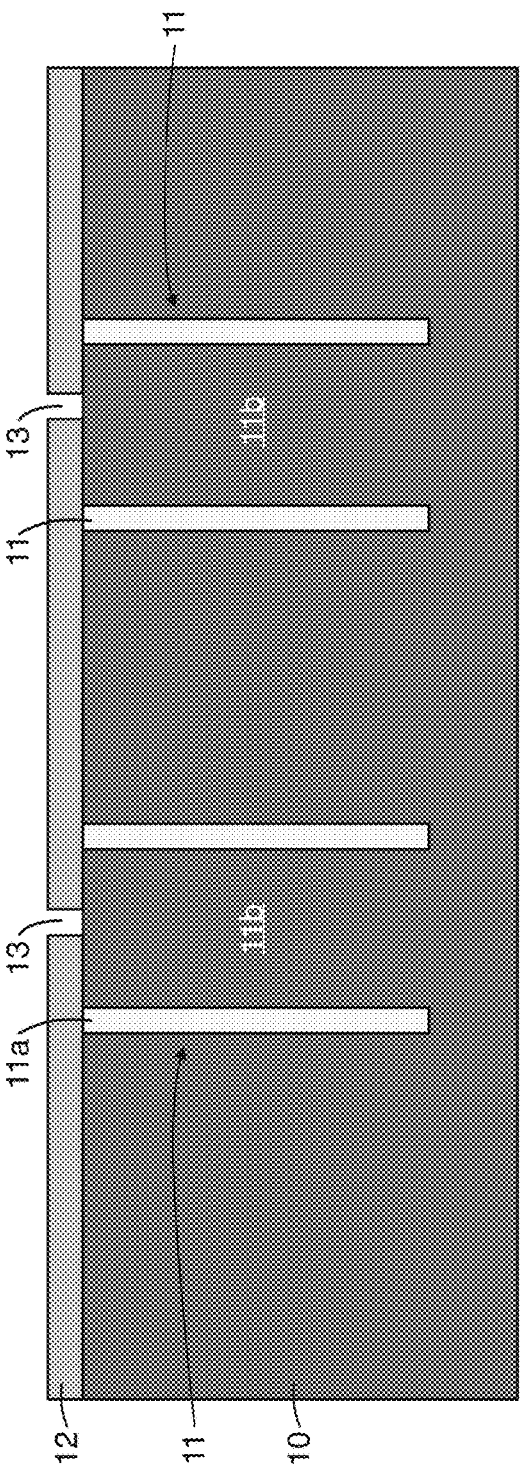

After this, deposition of a permanent oxide layer 12 over the top side of the substrate 10 is performed, as shown in FIG. 4. Holes 13 are defined in the oxide layer 12 over the inner layers 11*b* of the trenches 11.

Figure 5:
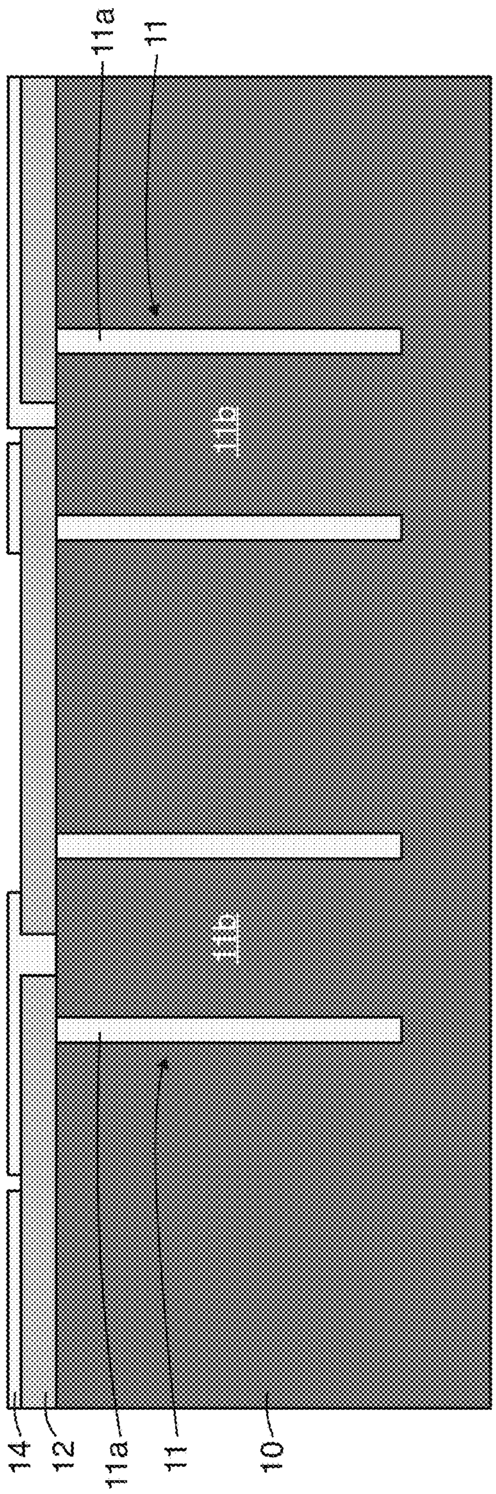
Figure 6:
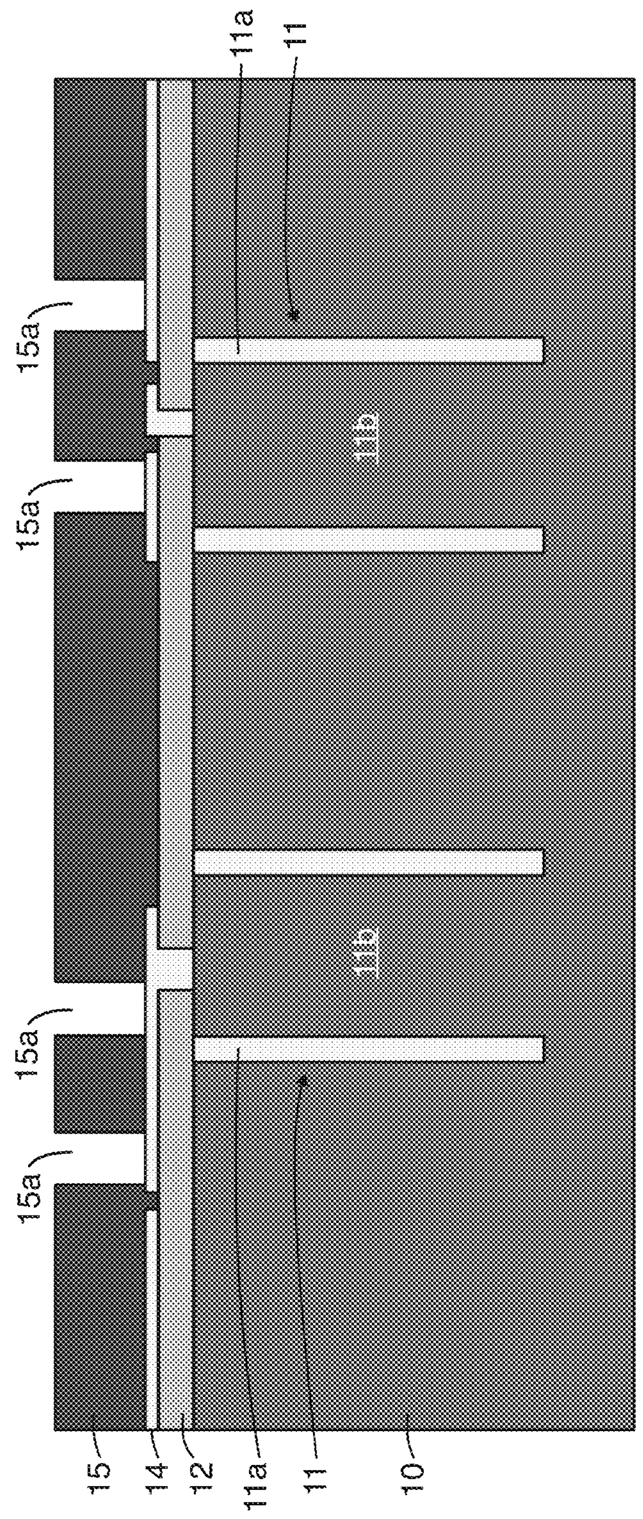

A conductive polysilicon runner layer 14 is then deposited and patterned to form an interconnection layer, as shown in FIG. 5. A sacrificial layer 15 (e.g., TEOS) is deposited on the interconnection layer 14 and exposed portions of the oxide layer 12, and is then patterned and planarized, as shown in FIG. 6. The patterning defines through-holes 15*a* in the sacrificial layer 15 positioned about what will be mechanical and electrical anchorage points for the membrane once formed.

Figure 7:
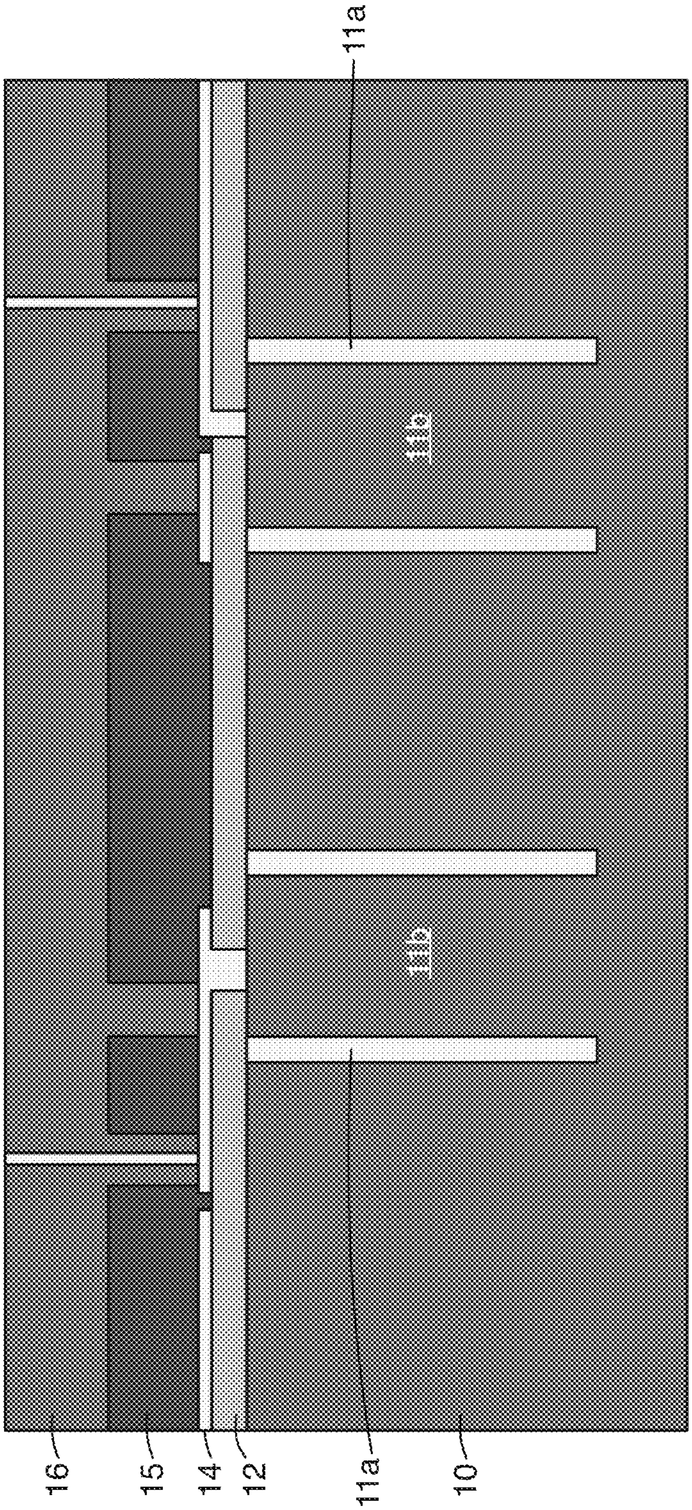
Figure 8:
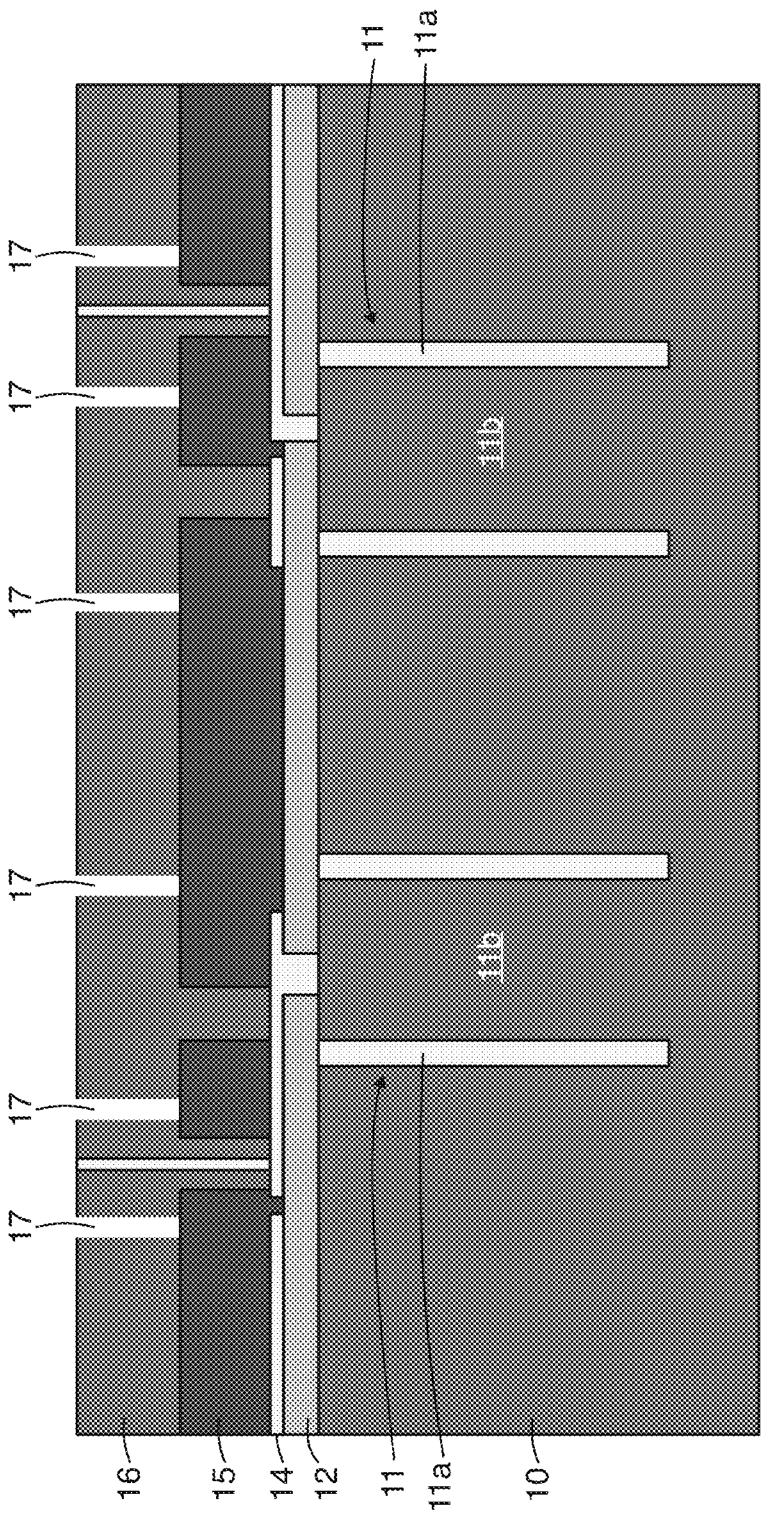
Figure 9:
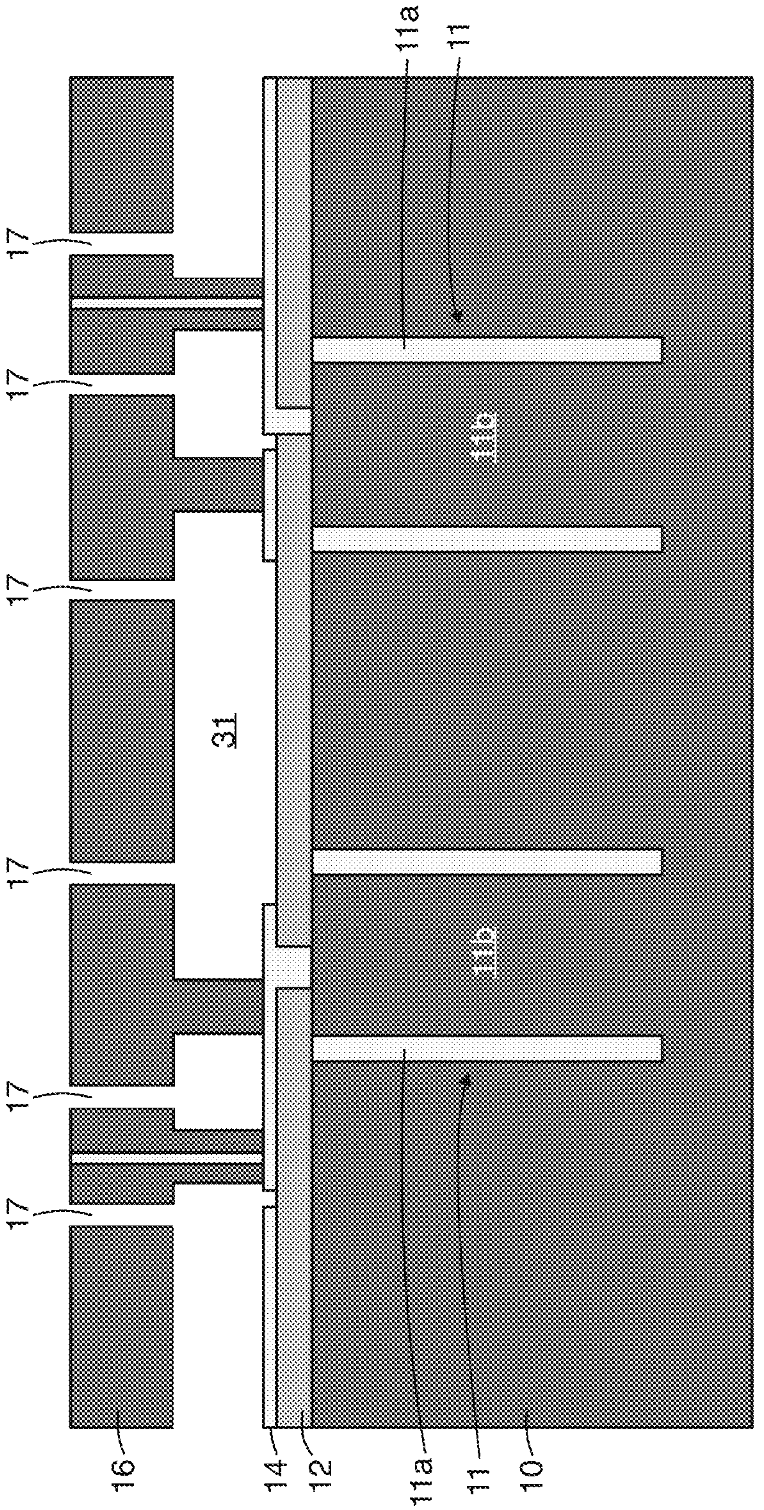

An epitaxial silicon layer 16 is grown over the sacrificial layer 15 and exposed portions of the interconnection layer 14 and then planarized, as shown in FIG. 7. This epitaxial silicon layer 16 will form the structural layer (e.g., the membrane). An etching is performed to form release trenches 17, as shown in FIG. 8. A vapor-phase hydrofluoric acid (vHF) etching, also referred to as a vHF release, is then performed to remove the sacrificial layer 15, forming the membrane 16 and yielding the cavity 31 under the membrane 16, as shown in FIG. 9. The cavity 31 permits movement of the membrane 16 to generate ultrasound waves.

Figure 10:
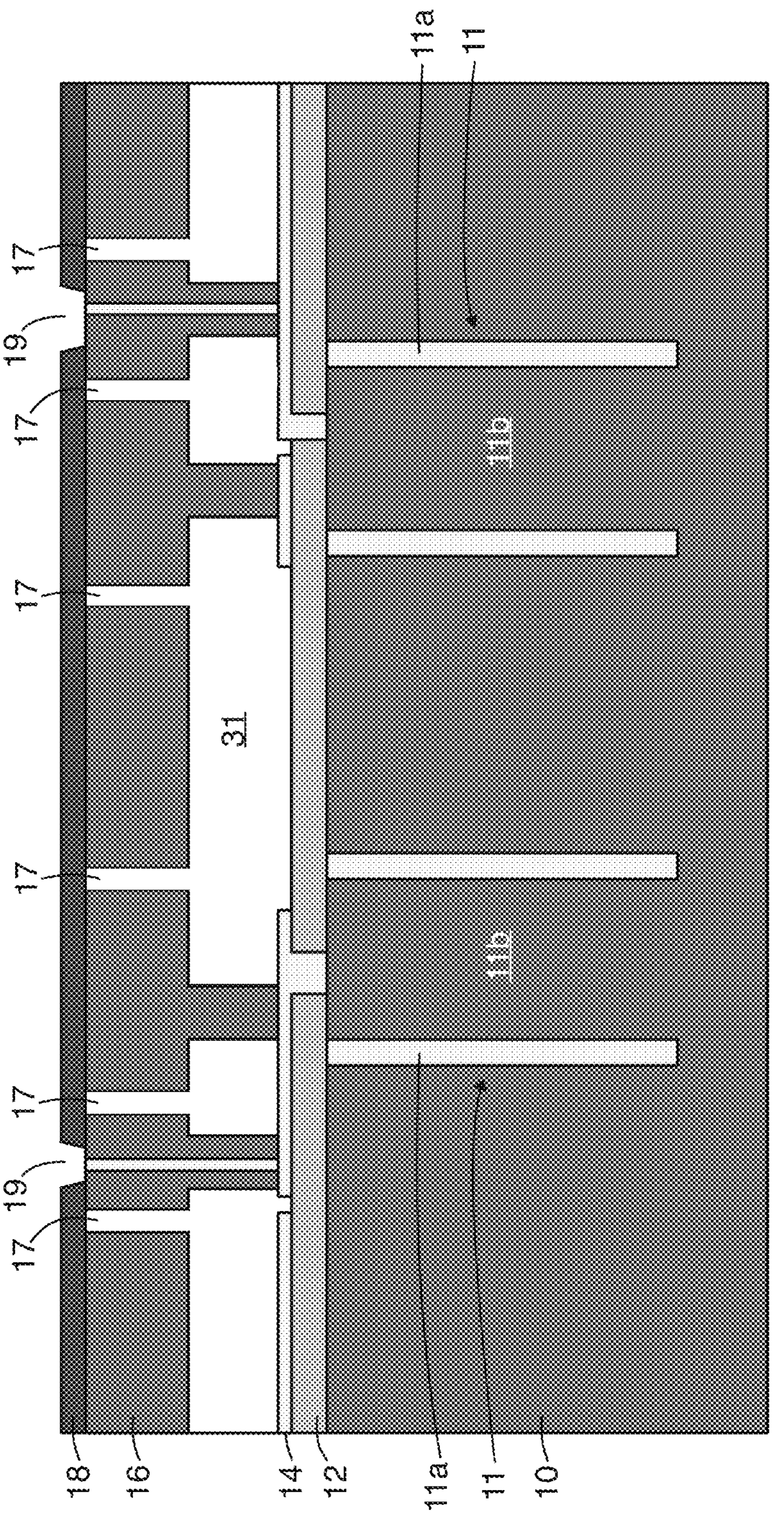

Then, a non-conformal chemical vapor deposition of a TEOS layer 18 is performed, the TEOS layer 18 serving to close off the openings of the trenches 17 adjacent the front face of the membrane 16, as shown in FIG. 10. As also shown in FIG. 10, the TEOS layer 18 is patterned, with through-holes 19 being formed therein.

Figure 11:
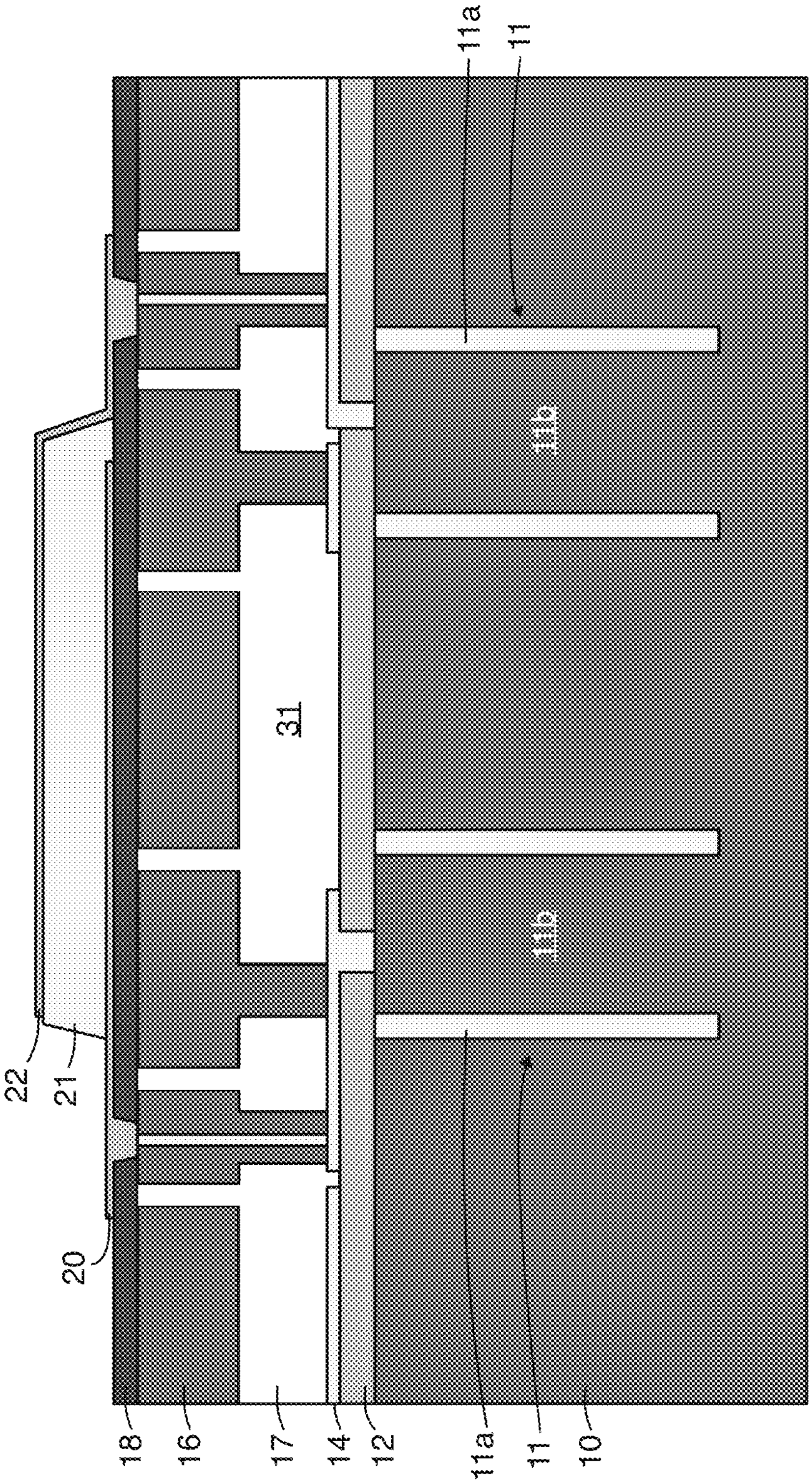

A piezoelectric stack is next formed on the TEOS layer 18, as shown in FIG. 11. Forming the piezoelectric stack includes forming the first electrode 20 on the TEOS layer 18 and extending through one of the through-holes 19 to contact the membrane 16 by deposition and patterning, forming the piezoelectric layer 21 over the front face of the first electrode 20 and past one side of the first electrode 20 to contact the front face of the TEOS layer 18 by deposition and patterning, and forming the second electrode 22 over the front face of the piezoelectric layer 21 and extending past one side of the piezoelectric layer 21 to contact the TEOS layer 18 and an exposed portion of the membrane 16 by deposition and patterning.

Figure 12:
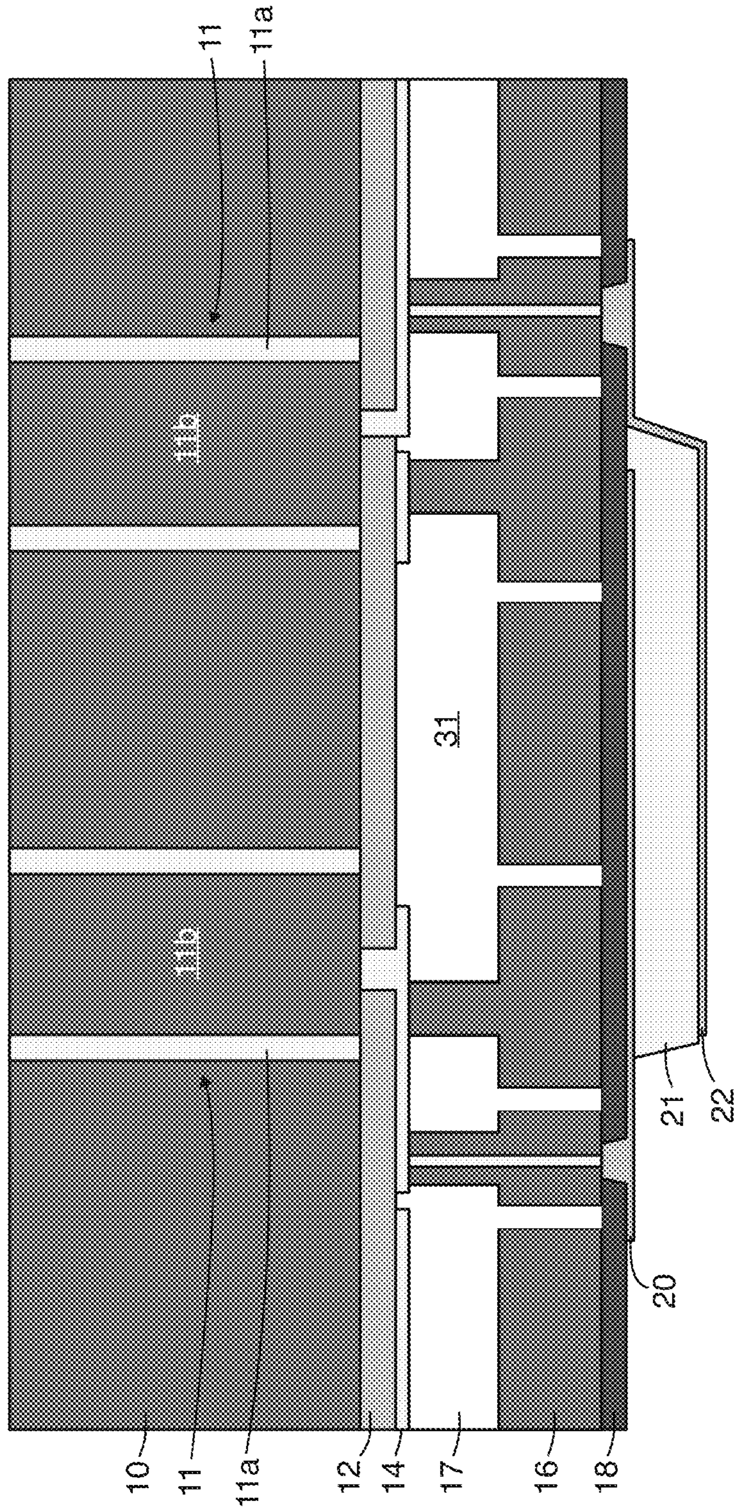
Figure 13:
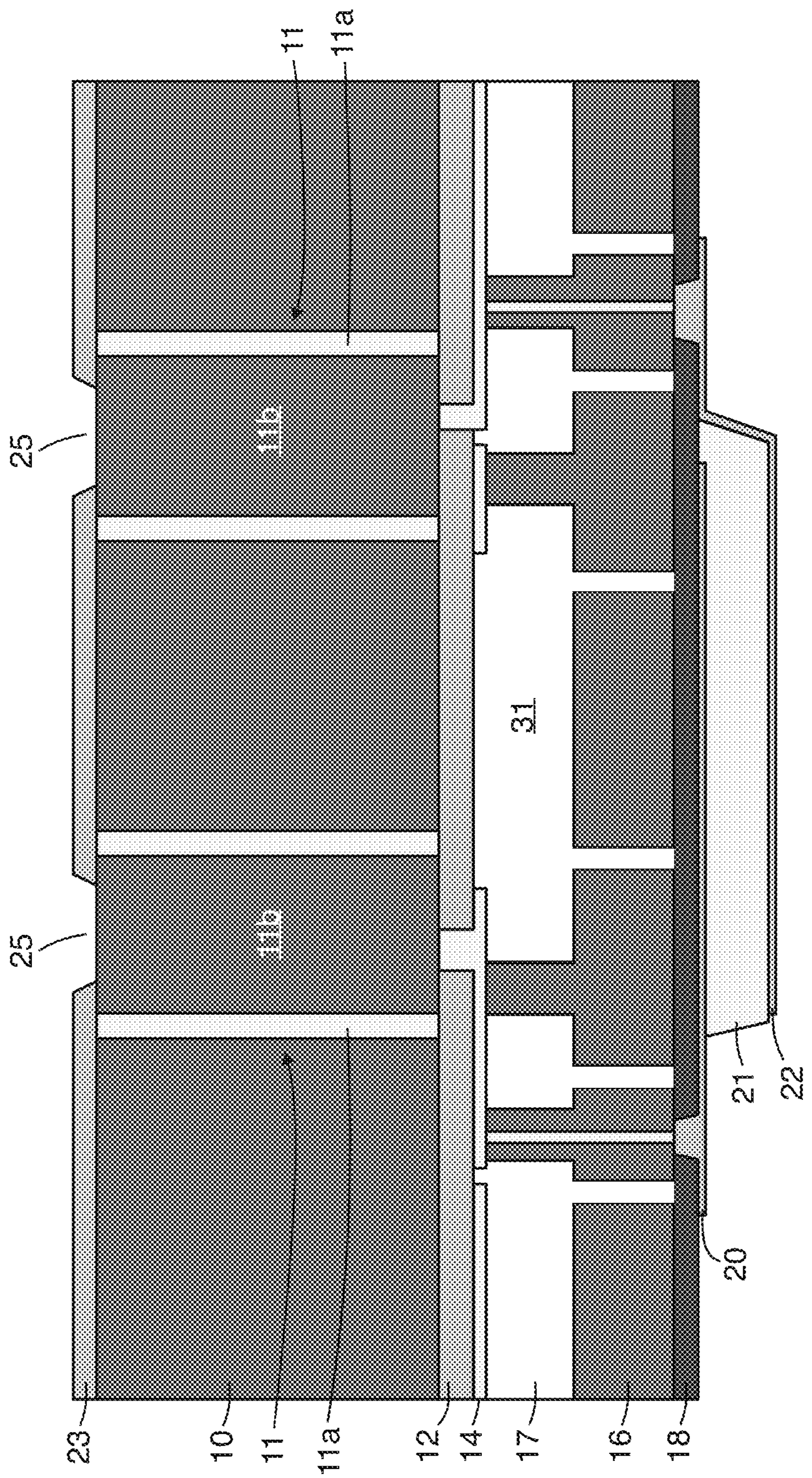

The device is then flipped and the back side of the substrate 10 is ground such that the vias 11 are exposed, as shown in FIG. 12. An oxide layer 23 is deposited on the back side of the substrate 10, as shown in FIG. 13, and patterned to form through-holes 25 therein over exposed portions of the vias 11. Back side electrodes 24 are then formed to extend through the through-holes to make physical and electrical contact with the inner layers 11*b* of the vias 11, producing the PMUT cell 5 shown in FIG. 1. These back side electrodes 24 are formed by deposition of a desired material and subsequent patterning.

Figure 14:
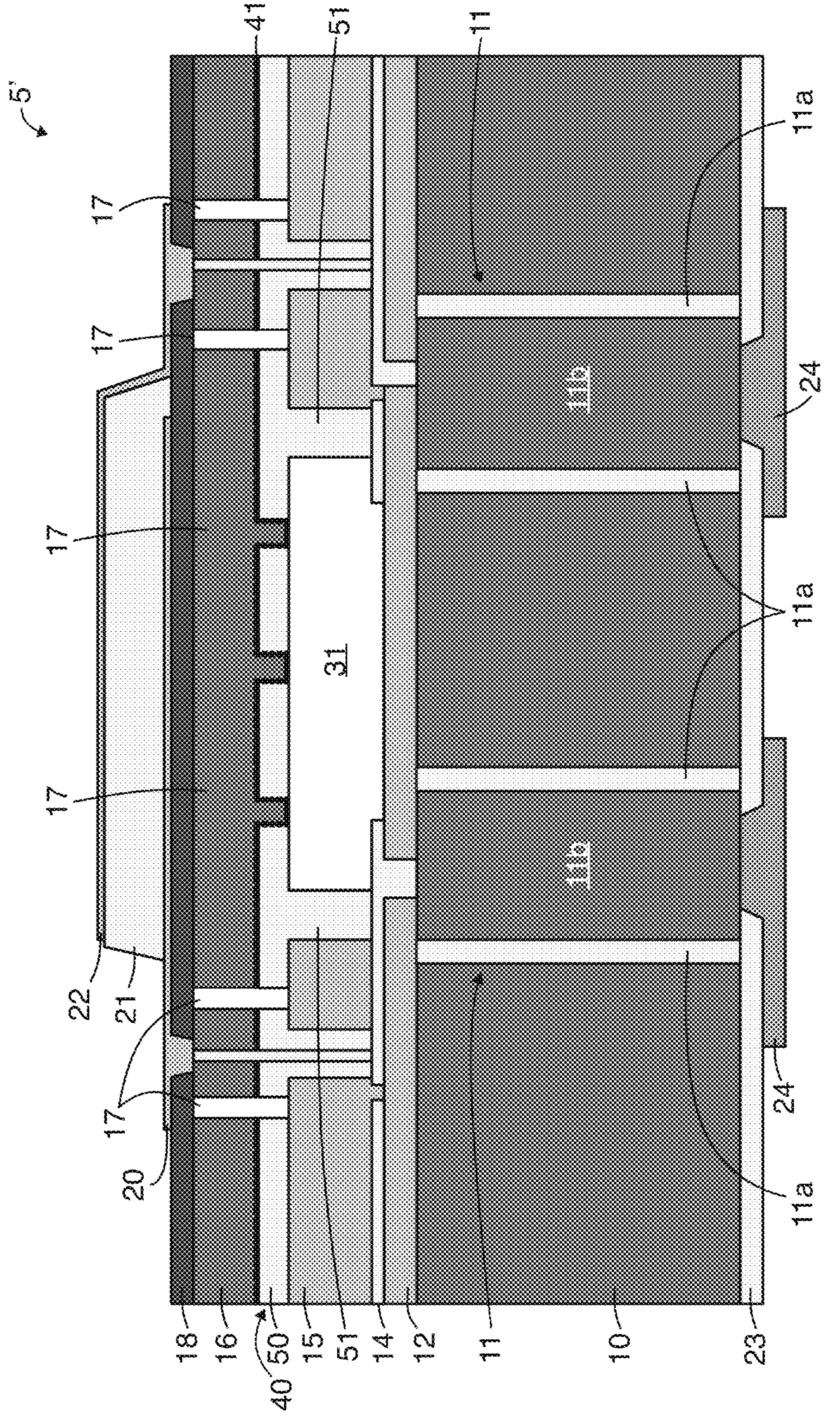
FIG. 14 is a cross sectional view of an alternative embodiment of piezoelectric micromachined ultrasound transducer (PMUT) cell disclosed herein.

Other embodiments of the PMUT cell 5' are envisioned. Refer now to FIG. 14. An alternative embodiment of the PMUT cell 5' includes a highly doped substrate 10 formed of, for example, red phosphorous, having vias 11 formed therein. The vias 11 are formed by insulating rings 11*a* surrounding portions of the substrate 10 acting as conductive columns 11*b*.

An oxide layer 12 is stacked on the front side of the substrate 10, with the back face of the oxide layer 12 being in direct physical contact with the front side of the substrate 10. An interconnection layer 14 is stacked on the oxide layer 12 such that its back face is in direct physical contact with the front face of the oxide layer 12. The oxide layer 12 has openings formed therein through which portions of the interconnection layer 14 extend to make direct physical and electrical contact with the conductive columns 11*b* of the vias 11.

A supporting layer 40 is carried by and in direct physical contact with remaining portions of the sacrificial layer 15 as well as exposed portions of the interconnection layer 14, with the bottom face of the supporting layer 40 being in direct physical contact with the top faces of the remaining portions of the sacrificial layer 15 as well as the top faces of exposed portions of the interconnection layer 14. Anchoring legs 51 of the supporting layer 40 extend downwardly from a main body 50 of the supporting layer 40 to make physical contact with the front face of the interconnection layer 14. A permeable polysilicon layer 41 is stacked on and in direct physical contact with the top face of the supporting layer 40. The anchoring legs 51 of the supporting layer 40 serve to space the main body 50 of the supporting layer 40 apart from the interconnection layer 14. A chamber 31 is defined between exposed portions of the front face of the oxide layer 12, associated parts of the front face of the interconnection layer 14, and back face of the main body 50 of the supporting layer 40. A structural layer 16 forming a membrane is carried by and in direct physical contact with the supporting layer 40.

A tetraethyl orthosilicate (TEOS) layer 18 is stacked on the front face of the membrane 16 such that its back face is in direct physical contact with the front face of the membrane 16 and covers through-holes 17 that are defined in the membrane 16 and the structural layer 40. A first electrode 20 is stacked on the front face of the TEOS layer 18, and through-holes are defined in the TEOS layer 18 such that portions of the first electrode 20 extend therethrough to contact underlying portions of the front face of the membrane 16. A piezoelectric layer 21 is stacked on and in direct physical contact with the front face of the first electrode 20 and an exposed portion of the front face of the TEOS layer 18. A second electrode 22 is stacked on and in direct physical contact with the piezoelectric layer 21, with a portion of the back face of the second electrode 22 being in direct physical contact with a front face of the piezoelectric layer 21, thereby sandwiching the piezoelectric layer 21 between the first electrode 20 and second electrode 22. A portion of the second electrode 22 extends past the side end of the piezoelectric layer 21 to make contact with the front face of the TEOS layer 18 and to extend through an exposed portion of the TEOS layer 18 to contact an underlying portion of the membrane 16.

An insulating layer 23 is stacked on the back side of the substrate 10 such that its back face is in direct physical contact with the back side of the substrate. Through-holes are defined in the insulating layer 23 through which back side electrodes 24 extend to make physical and electrical contact with the conductive columns 11*b* of the vias 11.

Figure 15:
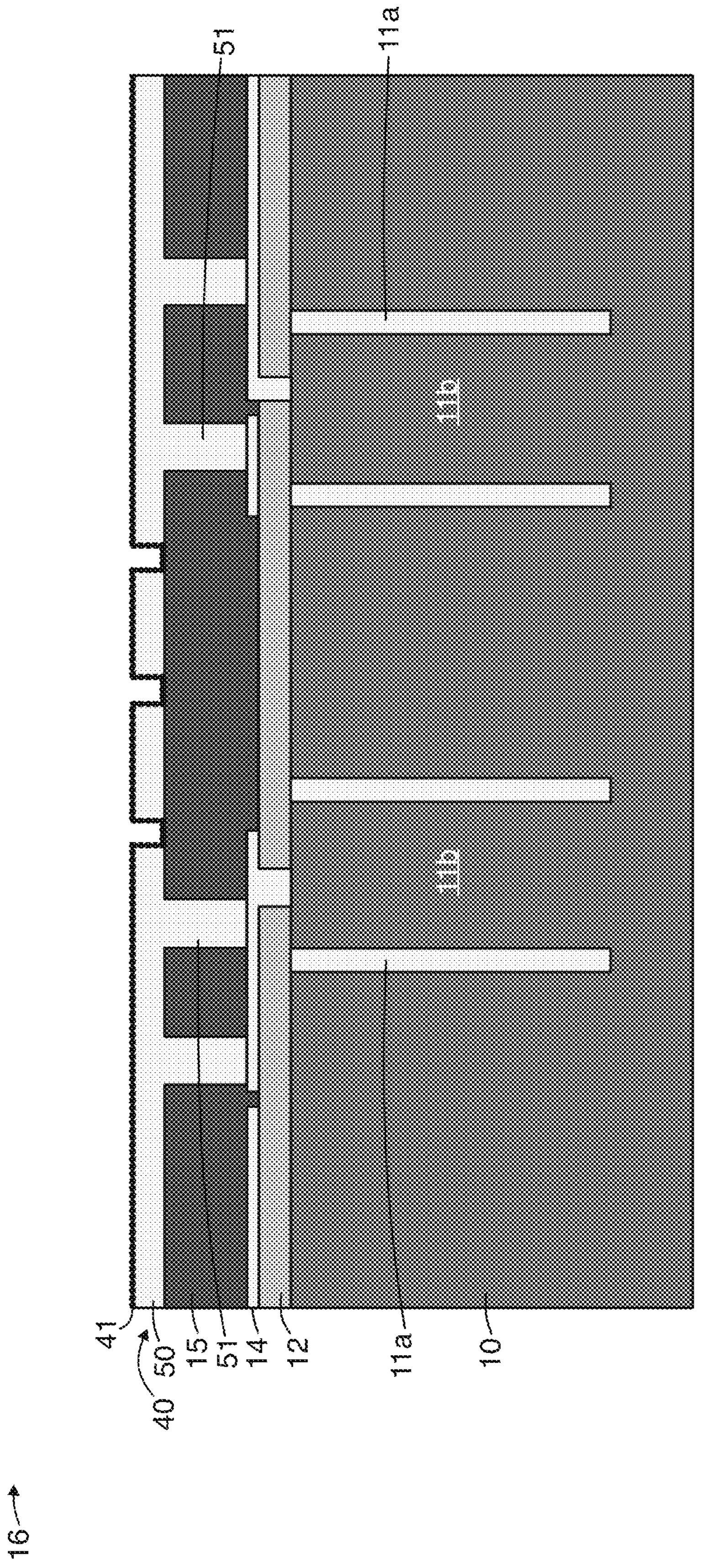
FIGS. 15-17 are a series of cross-sectional views showing the process flow steps for forming the PMUT cell of FIG. 14, with the illustrated process flow steps in FIGS. 15-17 being those that are different than those involved in the formation of the PMUT cell of FIG. 1.
Figure 16:
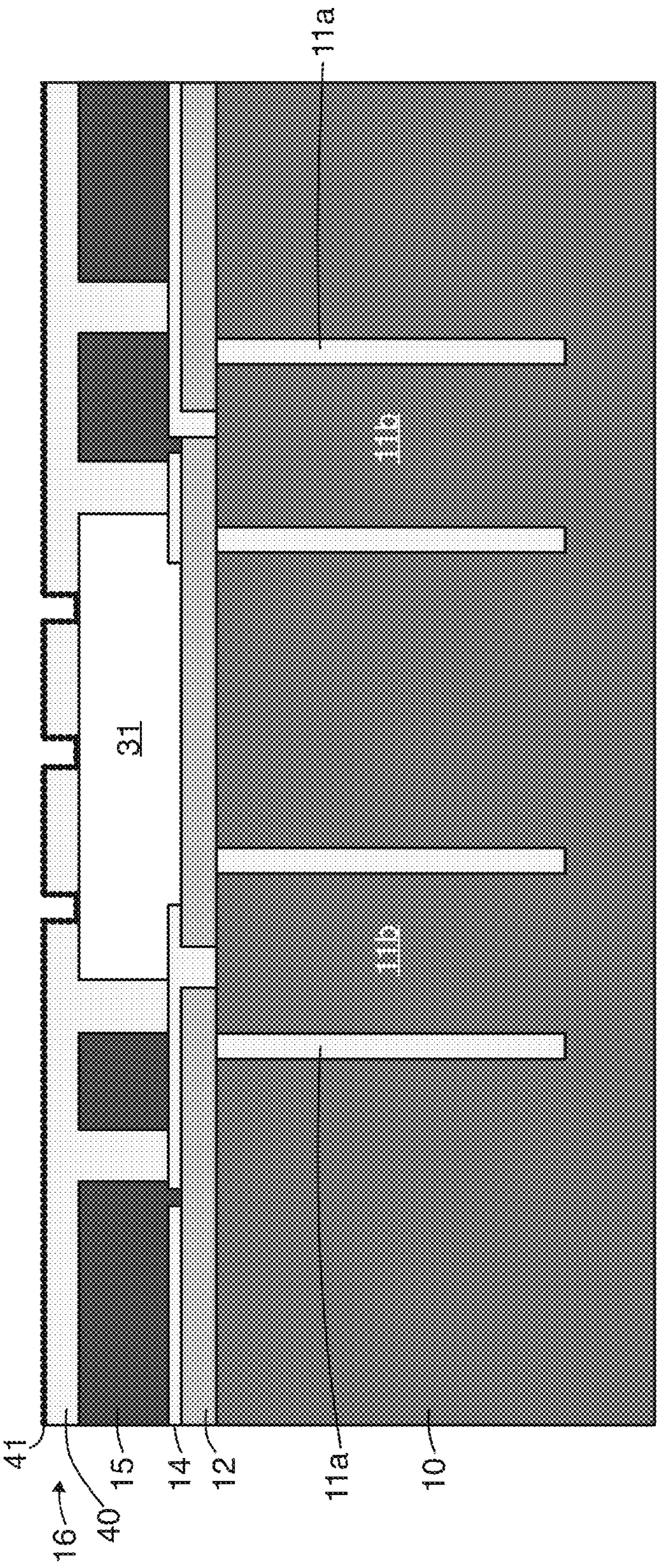
Figure 17:
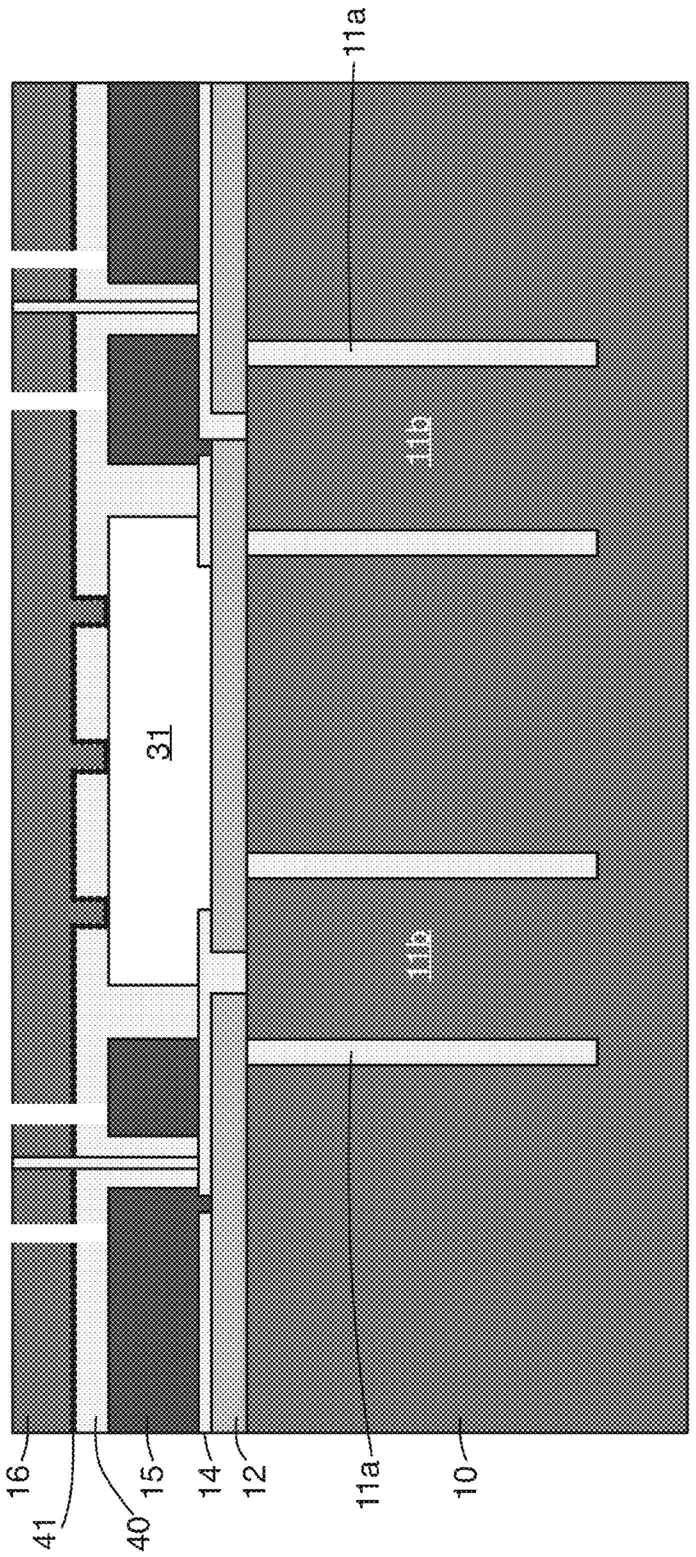

A process flow for forming the PMUT cells 5' is now described with initial reference to FIG. 15. Formation of the PMUT cells 5' proceeds as described above with reference to FIGS. 2-6 for formation of the PMUT cells 5 up through the formation and patterning of the sacrificial layer 15. After formation and patterning of the sacrificial layer 15, the structural layer 40 is formed and patterned, and the permeable polysilicon layer 41 is deposited, as shown in FIG. 15. A vHF release is then performed through the permeable polysilicon layer 41, etching away portions of the sacrificial layer 15 directly underlying and in contact with the permeable polysilicon layer 41, defining the chamber 31, as shown in FIG. 16. The structural layer 16 is epitaxially grown on the structural layer 40 and patterned, as shown in FIG. 17. Thereafter, the piezoelectric stack is formed as described above and the back side of the substrate 10 is ground and the back side electrodes are formed as described above.

It is clear that modifications and variations may be made to what has been described and illustrated herein, without thereby departing from the scope of this disclosure, as defined in the annexed claims.

While the disclosure has been described with respect to a limited number of embodiments, those skilled in the art, having benefit of this disclosure, will appreciate that other embodiments can be envisioned that do not depart from the scope of the disclosure as disclosed herein. Accordingly, the scope of the disclosure shall be limited only by the attached claims.

The invention claimed is:

1. A device comprising a piezoelectric micromachined ultrasound transducer (PMUT), the PMUT comprising:
- a substrate having a plurality of conductive vias formed therein, each conductive via comprised of a portion of the substrate extending completely from a back side of the substrate to a front side of the substrate and being encircled by an isolating structure that electrically isolates that portion of the substrate from other portions of the substrate;
- an insulating layer stacked on the front side of the substrate and having through-holes defined therein over the plurality of conductive vias;
- an interconnection layer stacked on the insulating layer and being directly electrically connected to the plurality of conductive vias;
- a membrane carried by the interconnection layer and underlying substrate, the membrane shaped so as to delimit a chamber defined on a top side and sidewalls by the membrane and defined on a bottom side by the insulating layer; and
- a piezoelectric stack formed on the membrane over the chamber and configured to vibrate the membrane in response to application of an alternating voltage to the piezoelectric stack.

2. The device of claim 1, wherein the substrate has a plurality of conductive columns formed therein, each conductive column being the portion of the substrate within each conductive via that extends completely from the back side of the substrate to the front side of the substrate and is encircled by the isolating structure.

3. The device of claim 2, wherein each conductive column is comprised of doped polysilicon.

4. The device of claim 2, wherein the isolating structure of each via is comprised of oxide.

5. The device of claim 1, wherein the insulating layer comprises an oxide layer.

6. The device of claim 1, wherein each PMUT further comprises an insulating layer on the back side of the substrate, with electrodes extending through holes in the insulating layer on the back side to contact the conductive vias.

7. The device of claim 1, further comprising first and second conventional vias formed to extend through the membrane to electrically connect the piezoelectric stack to the interconnection layer.

8. The device of claim 1, wherein the membrane comprises: a support layer carried by the interconnection layer and underlying substrate and being shaped so as to delimit the chamber; a permeable polysilicon layer formed on the support layer; and a structural layer carried by the permeable polysilicon layer and underlying portions of the structural layer.

9. The device of claim 8, further comprising a silicon thermal oxide layer stacked on the membrane and carrying the piezoelectric stack; wherein the piezoelectric stack comprises a first electrode formed on the silicon thermal oxide layer, a piezoelectric layer formed on the first electrode, and a second electrode formed on the piezoelectric layer; wherein the first electrode is electrically connected to the interconnection layer through a first conventional via extending through the membrane and silicon thermal oxide layer; and wherein the second electrode is electrically connected to the interconnection layer through a second conventional via extending through the membrane and silicon thermal oxide layer.

10. A device including a piezoelectric micromachined ultrasound transducer (PMUT) array, the device comprising:
- a substrate including a plurality of isolated conductive columns extending between a back side of the substrate and a front side of the substrate;
- a plurality of PMUT cells supported by the substrate, each PMUT cell including a membrane defining a respective cavity and a piezoelectric stack carried by the membrane; and
- an interconnection structure electrically coupling selected ones of the piezoelectric stacks of multiple PMUT cells to a common pair of isolated conductive columns of the plurality of isolated conductive columns such that the multiple PMUT cells are driven together by the common pair of the isolated conductive columns.

11. The device of claim 10, wherein the plurality of PMUT cells is arranged into unit cells, each unit cell including a first PMUT cell having electrical connection to the isolated conductive columns and one or more additional PMUT cells lacking direct connection to the isolated conductive columns and instead electrically connected through electrodes of the first PMUT cell.

12. The device of claim 11, wherein, within each unit cell, top electrodes of the additional PMUT cells are electrically connected to a top electrode of the first PMUT cell and bottom electrodes of the additional PMUT cells are electrically connected to a bottom electrode of the first PMUT cell.

13. The device of claim 11, wherein each unit cell is driven by a total of two isolated conductive columns of the plurality of isolated conductive columns.

14. The device of claim 10, wherein each isolated conductive column is formed from a portion of the substrate surrounded by an isolating ring, the isolating ring electrically isolating the portion of the substrate from adjacent portions of the substrate.

15. The device of claim 10, further comprising a plurality of back side electrodes formed on the back side of the substrate and extending through an insulating layer to contact respective isolated conductive columns of the plurality of isolated conductive columns.

16. The device of claim 10, wherein each PMUT cell further includes an interconnection layer positioned on the front side of the substrate, the interconnection layer being electrically coupled to isolated conductive columns and electrically coupling the isolated conductive columns to the piezoelectric stack of the PMUT cell.

17. The device of claim 16, wherein each PMUT cell further includes at least one conductive via extending through the membrane to connect the interconnection layer to an electrode of the piezoelectric stack.

18. The device of claim 10, wherein each membrane includes a support layer spaced from the interconnection structure to define the respective cavity and a structural layer carried by the support layer.

19. The device of claim 18, wherein each membrane further includes a permeable layer positioned between the support layer and the structural layer and configured to permit removal of a sacrificial material during formation of the cavity.

* * * * *